(12) United States Patent
Jacobs et al.

(10) Patent No.: US 7,585,646 B2
(45) Date of Patent: *Sep. 8, 2009

(54) HUMAN GIL-19/AE289 POLYNUCLEOTIDES AND METHODS OF PRODUCING THE ENCODED POLYPEPTIDES

(75) Inventors: Kenneth Jacobs, Newton, MA (US); Lynette Fouser, Acton, MA (US); Vikki Spaulding, Acton, MA (US); Dejun Xuan, Clayton, MI (US)

(73) Assignee: Genetics Institute, LLC, Cambridge, MA (US)

( * ) Notice: Subject to any disclaimer, the term of this patent is extended or adjusted under 35 U.S.C. 154(b) by 350 days.

This patent is subject to a terminal disclaimer.

(21) Appl. No.: 11/013,920

(22) Filed: Dec. 17, 2004

(65) Prior Publication Data

US 2005/0158760 A1 Jul. 21, 2005

Related U.S. Application Data

(63) Continuation of application No. 09/561,811, filed on Apr. 28, 2000, now Pat. No. 7,307,161.

(60) Provisional application No. 60/131,473, filed on Apr. 28, 1999.

(51) Int. Cl.
| | |
|---|---|
| C12P 21/06 | (2006.01) |
| C12N 1/20 | (2006.01) |
| C12N 15/00 | (2006.01) |
| C12N 5/00 | (2006.01) |
| C12N 5/02 | (2006.01) |
| C12N 15/74 | (2006.01) |
| C07H 21/04 | (2006.01) |

(52) U.S. Cl. .............. 435/69.1; 435/252.3; 435/320.1; 435/325; 435/471; 536/23.5

(58) Field of Classification Search .................. None
See application file for complete search history.

(56) References Cited

U.S. PATENT DOCUMENTS

| | | | |
|---|---|---|---|
| 5,350,836 | A | 9/1994 | Kopchick et al. |
| 5,536,637 | A | 7/1996 | Jacobs |
| 6,274,710 | B1 | 8/2001 | Dumoutier et al. |
| 6,331,613 | B1 | 12/2001 | Dumoutier et al. |
| 6,359,117 | B1 | 3/2002 | Dumoutier et al. |
| 6,551,799 | B2 | 4/2003 | Gurney et al. |
| 2001/0024652 | A1 | 9/2001 | Dumoutier et al. |
| 2002/0012669 | A1 | 1/2002 | Presnell et al. |
| 2002/0102723 | A1 | 8/2002 | Gurney et al. |
| 2002/0187523 | A1 | 12/2002 | Tang et al. |
| 2003/0012788 | A1 | 1/2003 | Renauld et al. |
| 2003/0170823 | A1 | 9/2003 | Presnell et al. |
| 2004/0023341 | A1 | 2/2004 | Xu et al. |
| 2004/0110189 | A1 | 6/2004 | Dumoutier et al. |
| 2004/0152125 | A1 | 8/2004 | Presnell et al. |
| 2004/0180399 | A1 | 9/2004 | Renauld et al. |

FOREIGN PATENT DOCUMENTS

| | | |
|---|---|---|
| WO | WO 94/01548 A2 | 1/1994 |
| WO | WO 99/61617 | 12/1999 |
| WO | WO 00/24758 | 5/2000 |
| WO | WO 00/70049 | 11/2000 |
| WO | WO 00/73457 | 12/2000 |
| WO | WO 00/77037 | 12/2000 |
| WO | WO 01/46422 | 6/2001 |
| WO | WO 02/10393 | 2/2002 |
| WO | WO02/16611 | 2/2002 |

OTHER PUBLICATIONS

R&D Systems, Catalog NR, AF582, XP002307633, "Anti-Mouse IL-22 Antibody," Aug. 22, 2002.

Kotenko, Sergei, "The Family of IL-10-Related Cytokines and Receptors: Related, But to What Extent?", Cytokine and Growth Factor Reviews, 13(3):223-240, Jun. 2002.

Radaeva, Svetlana, et al., "Interleukin 22 (IL-22) Plays a Protective Role in T Cell-Mediated Murine Hepatitis: IL-22 is a Survival Factor for Hepatocytes via STAT3 Activation," Hepatology, 39(5):1332-1342, May 2004.

Resmini, Christine, et al., "An Anti-Murine IL-22 Monoclonal Antibody Decreases Disease Severity in a Murine Model of Collagen Induced Arthritis," European Cytokine Network, 14(Supplement 3):129, Sep. 2003, and Annual Meeting of the International Cytokine Society; Dublin, Ireland, ISSN: 1148-5493, Sep. 20-24, 2003.

Li, J., et al., "Temporal Associations Between Interleukin 22 and the Extracellular Domains of IL-22R and IL-10R2," International Immunopharmacology, Elsevier, Amsterdam, NL, 4(5):693-708, May 2004.

Waterston, R., et al., GenBank Accession No. AC006734 for *Caenorhabditis elegans* clone 434B4, Feb. 25, 1999.

Wilson, R., et al., J. Mol. Biol., 261:155-172, 1996.

Bork et al., Trends in Genetics, 12:425-427, 1996.

Dumoutier et al., "Cloning and characterization of IL-10-related T cell-derived inducible factor (IL-TIF), a novel cytokine structurally related to IL-10 and inducible by IL-9," J. of Immunol., 164:1814-1819, 2000.

Syrbe et al., Springer Seminars in Immunopathology, 21:263-285, 1999.

Aoki, I., et al., "Comparison of the amino acid and nucleotide sequences between human and two guinea pig major basic proteins," FEBS Lett., 282(1):56-60, 1991.

Dumoutier, L., et al., "Human interleukin-10-related T cell-derived inducible factor: molecular cloning and functional characterization as an hepatocyte-stimulating factor," Proceedings of the National Academy of Sciences of USA, 97(18):10144-10149, 2000.

Dumoutier, L., et al., "IL-TIF/IL-21: genomic organization and mapping of the human and mouse genes," Genes Immun., 1:488-494, 2000.

(Continued)

Primary Examiner—Robert Landsman
(74) Attorney, Agent, or Firm—Lattimer, Mayberry & Matthews IP Law, LLP

(57) ABSTRACT

Novel human GIL-19/AE289 protein is disclosed which shows a high degree of homology to interleukin-10 (IL-10). Polynucleotides encoding such protein are also enclosed.

11 Claims, 1 Drawing Sheet

OTHER PUBLICATIONS

Dumoutier, L., et al., GenBank Accession No. NM_016971 for *Mus musculus* interleukin 10-related T cell-derived inducible factor (Iltif), Jun. 8, 2000.

Ozaki, T., et al., GenBank Accession No. D13973 for *Dictyostelium discoldeum* DNA for Dp87 protein, Feb. 1, 2000.

Aoki, I., et al., GenBank Accession No. P35709 for Eosinophil granule major basic protein 2 precursor (mbp-2), May 30, 2000.

Mahairas, G. G., et al., GenBank Accession No. AQ104025 for HS_3108_B1_C01_T7 CIT Approved Human Genomic Sperm Library D *Homo sapiens* genomic clone Plate=3108 Col=1 Row=F, Aug. 28, 1998.

Xie, M., et al., GenBank Accession No. AF279437 for *Homo sapiens* interleukin 22 (IL22), Oct. 9, 2000.

Dumoutier, L., et al., GenBank Accession No. AJ294727 for *Mus musculus* ILTIFa gene for IL TIF alpha protein (IL-22), exons 1a-5, Dec. 21, 2000.

Dumoutier, L., et al., GenBank Accession No. NP_065386 for Interleukin 22; interleukin 21; IL-10-related T-cell-derived inducible factor (*Homo sapiens*), Nov. 2, 2000.

Ozaki, T., et al., "Developmental regulation of transcription of a novel prespore-specific gene (Dp87) in *Dictyostelium discoideum*," Development, 1.17(4):1299-1308, 1993.

Sambrook, J., et al., Molecular Cloning. A laboratory manual, $2^{nd}$ ed., Cold Spring Harbor Laboratory Press, Ch. 17, 1989.

Xie, M. H., et al., "Interleukin (IL)-22, a novel human cytokine that signals through the interferon receptor-related proteins CRF2-4 and IL-22R," J. of Biol. Chem., 275(40):31335-31339, 2000.

Kotenko, Sergei V., et al., "Identification of the functional interleukin-22 (IL-22) receptor complex. The IL-10R2 chain (IL-10Rbeta) is a common chain of both the IL-10 and IL-22 (IL-10-related T cell-derived inducible factor, IL-TIF) receptor complexes," J. of Biol. Chem., 276(4):2725-2732, 2001.

Dumoutier, L., et al., "IL-TIF induces acute phase reactant production by hepatocytes through IL-10Rbeta," Immunology Letters, 73(2-3):261, 2000.

Lambert, A., et al., "Novel cytokine IL-22 administered by adenovirus vector or as recombinant purified protein induces acute-phase responses and renal tubular basophilia in female C57BL/6 mice," Toxicologic Pathology, 29:6:712, 2001.

Bork, P., Genome Research, 10:398-400, 2000.

Doerks et al., Trends in Genetics, 14:248-250, 1998.

Smith et al., Nature Biotechnology, 15:1222-1223, 1997.

Brenner, S.E., Trends in Genetics, 15:132-133, 1999.

Mahairas et al., PNAS USA, 96(17):9739-9744, 1999.

Vukicevic et al., PNAS USA, 93:9021-9026, 1996.

Massague, J. Cell., 49:437-438, 1987.

Pilbeam et al., Bone, 14:717-720, 1993.

Skolnick et al., Trends in Biotech., 18:34-39, 2000.

Species: Mus musculus Tissue: Spleen Cell Type: N/A

```
   1 GAATTCGGCC AAAGAGGCCT ACCTAAACAG GCTCTCCTCT CAGTTATCAA
  51 CTGTTGACAC TTGTGCGATC TCTGATGGCT GTCCTGCAGA AATCTATGAG
 101 TTTTTCCCTT ATGGGGACTT TGGCCGCCAG CTGCCTGCTT CTCATTGCCC
 151 TGTGGGCCCA GGAGGCAAAT GCGCTGCCCG TCAACACCCG GTGCAAGCTT
 201 GAGGTGTCCA ACTTCCAGCA GCCATACATC GTCAACCGCA CCTTTATGCT
 251 GGCCAAGGAG GCCAGCCTTG CAGATAACAA CACAGATGTC CGGCTCATCG
 301 GGGAGAAACT GTTCCGAGGA GTCAGTGCTA AGGATCAGTG CTACCTGATG
 351 AAGCAGGTGC TCAACTTCAC CCTGGAAGAC GTTCTGCTCC CCCAGTCAGA
 401 CAGGTTCCAG CCCTACATGC AGGAGGTGGT GCCTTTCCTG ACCAAACTCA
 451 GCAATCAGCT CAGCTCCTGT CACATCAGCG GTGACGACCA GAACATCCAG
 501 AAGAATGTCA GAAGGCTGAA GGAGACAGTG AAAAAGCTTG GAGAGAGTGG
 551 AGAGATCAAG GCGATTGGGG AACTGGACCT GCTGTTTATG TCTCTGAGAA
 601 ATGCTTGCGT CTGAGCGAGA AGAAGCTAGA AAACGAAGAA CTGCTCCTTC
 651 CTGCCTTCTA AAAAGAACAA TAAGATCCCT GAATGGACTT TTTTACTAAA
 701 GGAAAGTGAG AAGCTAACGT CCATCATTAT TAGAAGATTT CACATGAAAC
 751 CTGGCTCAGT TGAAAAGAA AATAGTGTCA AGTTGTCCAT GAGACCAGAG
 801 GTAGACTTGA TAACCACAAA GATTCATTGA CAATATTTTA TTGTCACTGA
 851 TGATACAACA GAAAAATAAT GTACTTTAAA AAATTGTTTG AAAGGAGGTT
 901 ACCTCTCATT CCTTTAGAAA AAAAGCTTAT GTAACTTCAT TTCCATAACC
 951 AATATTTTAT ATATGTAAGT TTATTTATTA TAAGTATACA TTTTATTTAT
1001 GTCAGTTTAT TAATATGGAT TTATTTATAG AAACATTATC TGCTATTGAT
1051 ATTTAGTATA AGGCAAATAA TATTTATGAC AATAACTATG GAAACAAGAT
1101 ATCTTAGGCT TTAATAAACA CATGGATATC ATAAAAAAAA AAAAAAAAAA
1151 AAAAAAAGC GGCCGC (SEQ ID NO:4)
```

FIG. 1

HUMAN GIL-19/AE289 POLYNUCLEOTIDES AND METHODS OF PRODUCING THE ENCODED POLYPEPTIDES

CROSS-REFERENCE TO RELATED APPLICATIONS

This is a continuation of application Ser. No. 09/561,811, filed Apr. 28, 2000, now U.S. Pat. No. 7,307,161, allowed, and claims the benefit of U.S. Provisional Application No. 60/131,473, filed Apr. 28, 1999, both of which are incorporated herein by reference.

FIELD OF THE INVENTION

The present invention provides novel proteins which show homology to interleukin-10 (IL-10) and polynucleotides encoding such proteins, along with therapeutic, diagnostic and research utilities for these polynucleotides and proteins.

BACKGROUND OF THE INVENTION

Technology aimed at the discovery of protein factors (including e.g., cytokines, such as lymphokines, interferons, CSFs and interleukins) has matured rapidly over the past decade. The now routine hybridization cloning and expression cloning techniques clone novel polynucleotides "directly" in the sense that they rely on information directly related to the discovered protein (i.e., partial DNA/amino acid sequence of the protein in the case of hybridization cloning; activity of the protein in the case of expression cloning). More recent "indirect" cloning techniques such as signal sequence cloning, which isolates DNA sequences based on the presence of a now well-recognized secretory leader sequence motif, as well as various PCR-based or low stringency hybridization cloning techniques, have advanced the state of the art by making available large numbers of DNA/amino acid sequences for proteins that are known to have biological activity by virtue of their secreted nature in the case of leader sequence cloning, or by virtue of the cell or tissue source in the case of PCR-based techniques. It is to these proteins and the polynucleotides encoding them that the present invention is directed.

SUMMARY OF THE INVENTION

In one embodiment, the present invention provides a composition comprising an isolated polynucleotide selected from the group consisting of:
 (a) a polynucleotide comprising the nucleotide sequence of SEQ ID NO:1;
 (b) a polynucleotide comprising the nucleotide sequence of SEQ ID NO: 1 from nucleotide 65 to nucleotide 601;
 (c) a polynucleotide comprising the nucleotide sequence of the full-length protein coding sequence of clone hGIL-19/AE289 deposited under accession number ATCC 207231;
 (d) a polynucleotide encoding the full-length protein encoded by the cDNA insert of clone hGIL-19/AE289 deposited under accession number ATCC 207231;
 (e) a polynucleotide comprising the nucleotide sequence of a mature protein coding sequence of clone hGIL-19/AE289 deposited under accession number ATCC 207231;
 (f) a polynucleotide encoding a mature protein encoded by the cDNA insert of clone hGIL-19/AE289 deposited under accession number ATCC 207231;
 (g) a polynucleotide encoding a protein comprising the amino acid sequence of SEQ ID NO:2;
 (h) a polynucleotide encoding a protein comprising a fragment of the amino acid sequence of SEQ ID NO:2 having biological activity, the fragment comprising eight contiguous amino acids of SEQ ID NO:2;
 (i) a polynucleotide which is an allelic variant of a polynucleotide of (a)-(f) above;
 (j) a polynucleotide which encodes a species homologue of the protein of (g) or (h) above;
 (k) a polynucleotide that hybridizes under stringent conditions to any one of the polynucleotides specified in (a)-(h); and
 (l) a polynucleotide that hybridizes under stringent conditions to any one of the polynucleotides specified in (a)-(h) and that has a length that is at least 25% of the length of SEQ ID NO:1.

Preferably, such polynucleotide comprises the nucleotide sequence of SEQ ID NO:1 from nucleotide 65 to nucleotide 601; the nucleotide sequence of the full-length protein coding sequence of clone hGIL-19/AE289 deposited under accession number ATCC 207231; or the nucleotide sequence of a mature protein coding sequence of clone hGIL-19/AE289 deposited under accession number ATCC 207231 (e.g., nucleotides 1-1177 of SEQ ID NO:1). In other preferred embodiments, the polynucleotide encodes the full-length or a mature protein encoded by the cDNA insert of clone hGIL-19/AE289 deposited under accession number ATCC 207231 (e.g., amino acids 1-179 of SEQ ID NO: 2). In further preferred embodiments, the present invention provides a polynucleotide encoding a protein comprising a fragment of the amino acid sequence of SEQ ID NO:2 having biological activity, the fragment preferably comprising eight (more preferably twenty, most preferably thirty) contiguous amino acids of SEQ ID NO:2, or a polynucleotide encoding a protein comprising a fragment of the amino acid sequence of SEQ ID NO:2 having biological activity, the fragment comprising the amino acid sequence from amino acid 84 to amino acid 93 of SEQ ID NO:2.

Other embodiments provide the gene corresponding to the cDNA sequence of SEQ ID NO:1.

Further embodiments of the invention provide isolated polynucleotides produced according to a process selected from the group consisting of:
 (a) a process comprising the steps of:
  (i) preparing one or more polynucleotide probes that hybridize in 6×SSC at 65 degrees C. to a nucleotide sequence selected from the group consisting of:
   (aa) SEQ ID NO:1, but excluding the poly(A) tail at the 3' end of SEQ ID NO:1; and
   (ab) the nucleotide sequence of the cDNA insert of clone hGIL-19/AE289 deposited under accession number ATCC 207231;
  (ii) hybridizing said probe(s) to human genomic DNA in conditions at least as stringent as 4×SSC at 50 degrees C.; and
  (iii) isolating the DNA polynucleotides detected with the probe(s);
 and
 (b) a process comprising the steps of:
  (i) preparing one or more polynucleotide primers that hybridize in 6×SSC at 65 degrees C. to a nucleotide sequence selected from the group consisting of:
   (ba) SEQ ID NO:1, but excluding the poly(A) tail at the 3' end of SEQ ID NO:1; and (bb) the nucleotide sequence of the cDNA insert of clone hGIL-19/AE289 deposited under accession number ATCC 207231;
(ii) hybridizing said primer(s) to human genomic DNA in conditions at least as stringent as 4×SSC at 50 degrees C.;
(iii) amplifying human DNA sequences; and
(iv) isolating the polynucleotide products of step (b)(iii).

Preferably the polynucleotide isolated according to the above process comprises a nucleotide sequence corresponding to the cDNA sequence of SEQ ID NO:1, and extending contiguously from a nucleotide sequence corresponding to the 5' end of SEQ ID NO:1 to a nucleotide sequence corresponding to the 3' end of SEQ ID NO:1, but excluding the poly(A) tail at the 3' end of SEQ ID NO:1. Also preferably the polynucleotide isolated according to the above process comprises a nucleotide sequence corresponding to the cDNA sequence of SEQ ID NO:1 from nucleotide 65 to nucleotide 601, and extending contiguously from a nucleotide sequence corresponding to the 5' end of said sequence of SEQ ID NO:1 from nucleotide 65 to nucleotide 601, to a nucleotide sequence corresponding to the 3' end of said sequence of SEQ ID NO:1 from nucleotide 65 to nucleotide 601.

In other embodiments, the present invention provides a composition comprising a protein, wherein said protein comprises an amino acid sequence selected from the group consisting of:
(a) the amino acid sequence of SEQ ID NO:2;
(b) a fragment of the amino acid sequence of SEQ ID NO:2, the fragment comprising eight contiguous amino acids of SEQ ID NO:2; and
(c) the amino acid sequence encoded by the cDNA insert of clone hGIL-19/AE289 deposited under accession number ATCC 207231;

the protein being substantially free from other mammalian proteins. Preferably such protein comprises the amino acid sequence of SEQ ID NO:2. In further preferred embodiments, the present invention provides a protein comprising a fragment of the amino acid sequence of SEQ ID NO:2 having biological activity, the fragment preferably comprising eight (more preferably twenty, most preferably thirty) contiguous amino acids of SEQ ID NO:2.

In certain preferred embodiments, the polynucleotide is operably linked to an expression control sequence. The invention also provides a host cell, including bacterial, yeast, insect and mammalian cells, transformed with such polynucleotide compositions. Also provided by the present invention are organisms that have enhanced, reduced, or modified expression of the gene(s) corresponding to the polynucleotide sequences disclosed herein.

Processes are also provided for producing a protein, which comprise:
(a) growing a culture of the host cell transformed with such polynucleotide compositions in a suitable culture medium; and
(b) purifying the protein from the culture.

The protein produced according to such methods is also provided by the present invention.

Protein compositions of the present invention may further comprise a pharmaceutically acceptable carrier. Compositions comprising an antibody which specifically reacts with such protein are also provided by the present invention.

Methods are also provided for preventing, treating or ameliorating a medical condition which comprises administering to a mammalian subject a therapeutically effective amount of a composition comprising a protein of the present invention and a pharmaceutically acceptable carrier.

BRIEF DESCRIPTION OF THE DRAWINGS

FIG. 1 depicts the sequence of the murine GIL-19 cDNA.

DETAILED DESCRIPTION

Isolated Proteins and Polynucleotides

Nucleotide and amino acid sequences, as presently determined, are reported below for each clone and protein disclosed in the present application. The nucleotide sequence of each clone can readily be determined by sequencing of the deposited clone in accordance with known methods. The predicted amino acid sequence (both full-length and mature forms) can then be determined from such nucleotide sequence. The amino acid sequence of the protein encoded by a particular clone can also be determined by expression of the clone in a suitable host cell, collecting the protein and determining its sequence.

As used herein a "secreted" protein is one which, when expressed in a suitable host cell, is transported across or through a membrane, including transport as a result of signal sequences in its amino acid sequence. "Secreted" proteins include without limitation proteins secreted wholly (e.g., soluble proteins) or partially (e.g., receptors) from the cell in which they are expressed. "Secreted" proteins also include without limitation proteins which are transported across the membrane of the endoplasmic reticulum.

Clone "hGIL-19/AE289"

A polynucleotide of the present invention has been identified initially as clone "hTIF/AE289", later renamed and referred to herein also as "hGIL-19/AE289" and "hGIL-19". Clone hGIL-19/AE289 was isolated according to the following method. A murine EST was identified from a murine cDNA library made from splenocytes activated with both ConA and bone marrow derived dendritic cells. The EST was identified using methods which are selective for cDNAs encoding secreted proteins (see U.S. Pat. No. 5,536,637). The murine EST sequence was used to isolate a full-length murine clone from the same cDNA library (SEQ ID NO:4; FIG. 1 depicts the sequence of the murine GIL-19 cDNA). Analysis of the sequence of the murine clone revealed a significant homology to interleukin-10 (IL-10).

In order to isolate a human homolog of the murine clone, PCR primers were constructed based upon the region of the murine sequence which showed homology to IL-10. Use of such primers for amplification in a human PBMC library produced a PCR product of significant size. Analysis of the sequence of the PCR product confirmed that it was a homolog of the murine cDNA. Oligonucleotides were constructed from the sequence of the partial human clone and used to isolate a full-length human clone from the PBMC library.

hGIL-19/AE289 is a full-length human clone, including the entire coding sequence of a secreted protein (also referred to herein as "hTIF/AE289 protein," "hGIL-19/AE289 protein" and "hGIL-19 protein"). Analysis of its sequence confirms its homology to IL-10.

The nucleotide sequence of hGIL-19 as presently determined is reported in SEQ ID NO:1, and includes a poly(A) tail. The open reading frame and the amino acid sequence of full-length hGIL-19 protein corresponding to the foregoing nucleotide sequence is reported in SEQ ID NO:2. The amino acid sequence of mature hGIL-19 corresponds to amino acids 34-179 of SEQ ID NO:2.

Clone "hGIL-19/AE289" was deposited on Apr. 28, 1999 with the American Type Culture Collection (10801 University Boulevard, Manassas, Va. 20110-2209 U.S.A.) as an original deposit under the Budapest Treaty and were given the accession number ATCC 207231. All restrictions on the availability to the public of the deposited material will be irrevocably removed upon the granting of the patent, except for the requirements specified in 37 C.F.R. § 1.808(b), and the term of the deposit will comply with 37 C.F.R. § 1.806.

Fragments of the proteins of the present invention (e.g. fragments which are capable of exhibiting biological activity) are also encompassed by the present invention. Fragments of the protein may be in linear form or they may be cyclized using known methods, for example, as described in H. U. Saragovi, et al., Bio/Technology 10, 773-778 (1992) and in R. S. McDowell, et al., J. Amer. Chem. Soc. 114, 9245-9253 (1992), both of which are incorporated herein by reference. Such fragments may be fused to carrier molecules such as immunoglobulins for many purposes, including increasing the valency of protein binding sites. For example, fragments of the protein may be fused through "linker" sequences to the Fc portion of an immunoglobulin. For a bivalent form of the protein, such a fusion could be to the Fc portion of an IgG molecule. Other immunoglobulin isotypes may also be used to generate such fusions. For example, a protein—IgM fusion would generate a decavalent form of the protein of the invention.

The present invention also provides both full-length and mature forms of the disclosed proteins. The full-length form of the such proteins is identified in the sequence listing by translation of the nucleotide sequence of each disclosed clone. The mature form(s) of such protein may be obtained by expression of the disclosed full-length polynucleotide (preferably those deposited with ATCC) in a suitable mammalian cell or other host cell. The sequence(s) of the mature form(s) of the protein may also be determinable from the amino acid sequence of the full-length form and are set forth herein, for example as amino acids 1-179 of SEQ ID NO:2.

The present invention also provides genes corresponding to the polynucleotide sequences disclosed herein. "Corresponding genes" are the regions of the genome that are transcribed to produce the mRNAs from which cDNA polynucleotide sequences are derived and may include contiguous regions of the genome necessary for the regulated expression of such genes. Corresponding genes may therefore include but are not limited to coding sequences, 5' and 3' untranslated regions, alternatively spliced exons, introns, promoters, enhancers, and silencer or suppressor elements. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials. An "isolated gene" is a gene that has been separated from the adjacent coding sequences, if any, present in the genome of the organism from which the gene was isolated.

The chromosomal location corresponding to the polynucleotide sequences disclosed herein may also be determined, for example by hybridizing appropriately labeled polynucleotides of the present invention to chromosomes in situ. It may also be possible to determine the corresponding chromosomal location for a disclosed polynucleotide by identifying significantly similar nucleotide sequences in public databases, such as expressed sequence tags (ESTs), that have already been mapped to particular chromosomal locations. For at least some of the polynucleotide sequences disclosed herein, public database sequences having at least some similarity to the polynucleotide of the present invention have been listed by database accession number. Searches using the GenBank accession numbers of these public database sequences can then be performed at an Internet site provided by the National Center for Biotechnology Information, in order to identify "UniGene clusters" of overlapping sequences. Many of the "UniGene clusters" of overlapping sequences so identified will already have been mapped to particular chromosomal sites.

Organisms that have enhanced, reduced, or modified expression of the gene(s) corresponding to the polynucleotide sequences disclosed herein are provided. The desired change in gene expression can be achieved through the use of antisense polynucleotides or ribozymes that bind and/or cleave the mRNA transcribed from the gene (Albert and Morris, 1994, *Trends Pharmacol. Sci.* 15(7): 250-254; Lavarosky et al., 1997, *Biochem. Mol. Med* 62(1): 11-22; and Hampel, 1998, *Prog. Nucleic Acid Res. Mol. Biol.* 58: 1-39; all of which are incorporated by reference herein). Transgenic animals that have multiple copies of the gene(s) corresponding to the polynucleotide sequences disclosed herein, preferably produced by transformation of cells with genetic constructs that are stably maintained within the transformed cells and their progeny, are provided. Transgenic animals that have modified genetic control regions that increase or reduce gene expression levels, or that change temporal or spatial patterns of gene expression, are also provided (see European Patent No. 0 649 464 B1, incorporated by reference herein). In addition, organisms are provided in which the gene(s) corresponding to the polynucleotide sequences disclosed herein have been partially or completely inactivated, through insertion of extraneous sequences into the corresponding gene(s) or through deletion of all or part of the corresponding gene(s). Partial or complete gene inactivation can be accomplished through insertion, preferably followed by imprecise excision, of transposable elements (Plasterk, 1992, *Bioessays* 14(9): 629-633; Zwaal et al., 1993, *Proc. Natl. Acad. Sci. USA* 90(16): 7431-7435; Clark et al., 1994, *Proc. Natl. Acad. Sci. USA* 91(2): 719-722; all of which are incorporated by reference herein), or through homologous recombination, preferably detected by positive/negative genetic selection strategies (Mansour et al., 1988, *Nature* 336: 348-352; U.S. Pat. Nos. 5,464,764; 5,487,992; 5,627,059; 5,631,153; 5,614,396; 5,616,491; and 5,679,523; all of which are incorporated by reference herein). These organisms with altered gene expression are preferably eukaryotes and more preferably are mammals. Such organisms are useful for the development of non-human models for the study of disorders involving the corresponding gene(s), and for the development of assay systems for the identification of molecules that interact with the protein product(s) of the corresponding gene(s).

Where the protein of the present invention is membrane-bound (e.g., is a receptor), the present invention also provides for soluble forms of such protein. In such forms, part or all of the intracellular and transmembrane domains of the protein are deleted such that the protein is fully secreted from the cell in which it is expressed. The intracellular and transmembrane domains of proteins of the invention can be identified in accordance with known techniques for determination of such domains from sequence information. For example, the Top-PredII computer program can be used to predict the location of transmembrane domains in an amino acid sequence, domains which are described by the location of the center of the transmembrane domain, with at least ten transmembrane amino acids on each side of the reported central residue(s).

Proteins and protein fragments of the present invention include proteins with amino acid sequence lengths that are at least 25% (more preferably at least 50%, and most preferably at least 75%) of the length of a disclosed protein and have at least 60% sequence identity (more preferably, at least 75% identity; most preferably at least 90% or 95% identity) with that disclosed protein, where sequence identity is determined by comparing the amino acid sequences of the proteins when aligned so as to maximize overlap and identity while minimizing sequence gaps. Also included in the present invention are proteins and protein fragments that contain a segment preferably comprising 8 or more (more preferably 20 or more, most preferably 30 or more) contiguous amino acids that shares at least 75% sequence identity (more preferably, at least 85% identity; most preferably at least 95% identity) with any such segment of any of the disclosed proteins.

In another embodiment, proteins, protein fragments, and recombinant proteins of the present invention include those which can be identified based on the presence of at least one "hGIL-19/AE289 receptor-binding motif." As used herein, the term "hGIL-19/AE289 receptor-binding motif" includes amino acid sequences or residues which are important for binding of hGIL-19 to its requisite receptor. In a preferred embodiment, a hGIL-19 protein contains a hGIL-19/AE289 receptor-binding motif including about amino acids 50-60 of SEQ ID NO:2. In another embodiment, a GIL-19 protein contains a hGIL-19/AE289 receptor-binding motif including about amino acids 63-81 of SEQ ID NO:2. In yet another embodiment, a GIL-19 protein contains a hGIL-19/AE289 receptor-binding motif including about amino acids 168-177 of SEQ ID NO:2. In a preferred embodiment, a GIL-19 protein contains a hGIL-19/AE289 receptor-binding motif including at least one of amino acids 50-60, amino acids 63-81, and/or about amino acids 168-177 of SEQ ID NO:2.

In yet another embodiment, a hGIL-19/AE289 receptor binding motif has an amino acid sequence at least 95%, 96%, 97%, 98%, 99%, or more identical to an amino acid sequence selected from the group consisting of amino acids 50-60 of SEQ ID NO:2, amino acids 63-81 of SEQ ID NO:2, and amino acids 168-177 of SEQ ID NO:2.

In another embodiment, proteins, protein fragments, and recombinant proteins of the present invention include those which can be identified based on the presence of at least one, two, three, four or more sites for N-linked glycosylation.

In particular, sequence identity may be determined using WU-BLAST (Washington University BLAST) version 2.0 software, which builds upon WU-BLAST version 1.4, which in turn is based on the public domain NCBI-BLAST version 1.4 (Altschul and Gish, 1996, Local alignment statistics, Doolittle ed., *Methods in Enzymology* 266: 460-480; Altschul et al., 1990, Basic local alignment search tool, *Journal of Molecular Biology* 215: 403-410; Gish and States, 1993, Identification of protein coding regions by database similarity search, *Nature Genetics* 3: 266-272; Karlin and Altschul, 1993, Applications and statistics for multiple high-scoring segments in molecular sequences, *Proc. Natl. Acad. Sci. USA* 90: 5873-5877; all of which are incorporated by reference herein). WU-BLAST version 2.0 executable programs for several UNIX platforms can be downloaded from the Internet site provided by Washington University in St. Louis (WUSTL). The complete suite of search programs (BLASTP, BLASTN, BLASTX, TBLASTN, and TBLASTX) is provided at that site, in addition to several support programs. WU-BLAST 2.0 is copyrighted and may not be sold or redistributed in any form or manner without the express written consent of the author; but the posted executables may otherwise be freely used for commercial, nonprofit, or academic purposes. In all search programs in the suite —BLASTP, BLASTN, BLASTX, TBLASTN and TBLASTX —the gapped alignment routines are integral to the database search itself, and thus yield much better sensitivity and selectivity while producing the more easily interpreted output. Gapping can optionally be turned off in all of these programs, if desired. The default penalty (Q) for a gap of length one is Q=9 for proteins and BLASTP, and Q=10 for BLASTN, but may be changed to any integer value including zero, one through eight, nine, ten, eleven, twelve through twenty, twenty-one through fifty, fifty-one through one hundred, etc. The default per-residue penalty for extending a gap (R) is R=2 for proteins and BLASTP, and R=10 for BLASTN, but may be changed to any integer value including zero, one, two, three, four, five, six, seven, eight, nine, ten, eleven, twelve through twenty, twenty-one through fifty, fifty-one through one hundred, etc. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

Species homologues of the disclosed polynucleotides and proteins are also provided by the present invention. As used herein, a "species homologue" is a protein or polynucleotide with a different species of origin from that of a given protein or polynucleotide, but with significant sequence similarity to the given protein or polynucleotide. Preferably, polynucleotide species homologues have at least 60% sequence identity (more preferably, at least 75%, 80%, 85%, 90%, 95%, 99%) with the given polynucleotide, and protein species homologues have at least 30% sequence identity (more preferably, at least 45%, 50%, 55%, 60%, 65%, 70%, 75%, 80%, 85%, 90%) with the given protein, where sequence identity is determined by comparing the nucleotide sequences of the polynucleotides or the amino acid sequences of the proteins when aligned so as to maximize overlap and identity while minimizing sequence gaps. Species homologues may be isolated and identified by making suitable probes or primers from the sequences provided herein and screening a suitable nucleic acid source from the desired species. Preferably, species homologues are those isolated from mammalian species. Most preferably, species homologues are those isolated from certain mammalian species such as, for example, *Pan troglodytes, Gorilla gorilla, Pongo pygmaeus, Hylobates concolor, Macaca mulatta, Papio papio, Papio hamadryas, Cercopithecus aethiops, Cebus capucinus, Aotus trivirgatus, Sanguinus oedipus, Microcebus murinus, Mus musculus, Rattus norvegicus, Cricetulus griseus, Felis catus, Mustela vison, Canis familiaris, Oryctolagus cuniculus, Bos taurus, Ovis aries, Sus scrofa,* and *Equus caballus,* for which genetic maps have been created allowing the identification of syntenic relationships between the genomic organization of genes in one species and the genomic organization of the related genes in another species (O'Brien and Seuánez, 1988, Ann. Rev. Genet. 22: 323-351; O'Brien et al., 1993, *Nature Genetics* 3:103-112; Johansson et al., 1995, *Genomics* 25: 682-690; Lyons et al., 1997, *Nature Genetics* 15: 47-56; O'Brien et al., 1997, *Trends in Genetics* 13(10): 393-399; Carver and Stubbs, 1997, *Genome Research* 7:1123-1137; all of which are incorporated by reference herein).

The invention also encompasses allelic variants of the disclosed polynucleotides or proteins; that is, naturally-occurring alternative forms of the isolated polynucleotides which also encode proteins which are identical or have significantly similar sequences to those encoded by the disclosed polynucleotides. Preferably, allelic variants have at least 60% sequence identity (more preferably, at least 75%, 80%, 85%, 90%, 95%, 99%) with the given polynucleotide, where sequence identity is determined by comparing the nucleotide sequences of the polynucleotides when aligned so as to maximize overlap and identity while minimizing sequence gaps. Allelic variants may be isolated and identified by making suitable probes or primers from the sequences provided herein and screening a suitable nucleic acid source from individuals of the appropriate species.

The invention also includes polynucleotides with sequences complementary to those of the polynucleotides disclosed herein.

The present invention also includes polynucleotides that hybridize under reduced stringency conditions, more preferably stringent conditions, and most preferably highly stringent conditions, to polynucleotides described herein. Examples of stringency conditions are shown in the table below: highly stringent conditions are those that are at least as stringent as, for example, conditions A-F; stringent conditions are at least as stringent as, for example, conditions G-L; and reduced stringency conditions are at least as stringent as, for example, conditions M-R.

ratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference.

Preferably, each such hybridizing polynucleotide has a length that is at least 25% (more preferably at least 50%, and most preferably at least 75%) of the length of the polynucleotide of the present invention to which it hybridizes, and has at least 60% sequence identity (more preferably, at least 75% identity; most preferably at least 90% or 95% identity) with the polynucleotide of the present invention to which it hybridizes, where sequence identity is determined by comparing the sequences of the hybridizing polynucleotides when aligned so as to maximize overlap and identity while minimizing sequence gaps.

The isolated polynucleotide of the invention may be operably linked to an expression control sequence such as the pMT2 or pED expression vectors disclosed in Kaufman et al., Nucleic Acids Res. 19, 4485-4490 (1991), in order to produce the protein recombinantly. Many suitable expression control

| Stringency Condition | Polynucleotide Hybrid | Hybrid Length (bp)‡ | Hybridization Temperature and Buffer† | Wash Temperature and Buffer† |
|---|---|---|---|---|
| A | DNA:DNA | ≧50 | 65° C.; 1xSSC -or- 42° C.; 1xSSC, 50% formamide | 65° C.; 0.3xSSC |
| B | DNA:DNA | <50 | $T_B$*; 1xSSC | $T_B$*; 1xSSC |
| C | DNA:RNA | ≧50 | 67° C.; 1xSSC -or- 45° C.; 1xSSC, 50% formamide | 67° C.; 0.3xSSC |
| D | DNA:RNA | <50 | $T_D$*; 1xSSC | $T_D$*; 1xSSC |
| E | RNA:RNA | ≧50 | 70° C.; 1xSSC -or- 50° C.; 1xSSC, 50% formamide | 70° C.; 0.3xSSC |
| F | RNA:RNA | <50 | $T_F$*; 1xSSC | $T_F$*; 1xSSC |
| G | DNA:DNA | ≧50 | 65° C.; 4xSSC -or- 42° C.; 4xSSC, 50% formamide | 65° C.; 1xSSC |
| H | DNA:DNA | <50 | $T_H$*; 4xSSC | $T_H$*; 4xSSC |
| I | DNA:RNA | ≧50 | 67° C.; 4xSSC -or- 45° C.; 4xSSC, 50% formamide | 67° C.; 1xSSC |
| J | DNA:RNA | <50 | $T_J$*; 4xSSC | $T_J$*; 4xSSC |
| K | RNA:RNA | ≧50 | 70° C.; 4xSSC -or- 50° C.; 4xSSC, 50% formamide | 67° C.; 1xSSC |
| L | RNA:RNA | <50 | $T_L$*; 2xSSC | $T_L$*; 2xSSC |
| M | DNA:DNA | ≧50 | 50° C.; 4xSSC -or- 40° C.; 6xSSC, 50% formamide | 50° C.; 2xSSC |
| N | DNA:DNA | <50 | $T_N$*; 6xSSC | $T_N$*; 6xSSC |
| O | DNA:RNA | ≧50 | 55° C.; 4xSSC -or- 42° C.; 6xSSC, 50% formamide | 55° C.; 2xSSC |
| P | DNA:RNA | <50 | $T_P$*; 6xSSC | $T_P$*; 6xSSC |
| Q | RNA:RNA | ≧50 | 60° C.; 4xSSC -or- 45° C.; 6xSSC, 50% formamide | 60° C.; 2xSSC |
| R | RNA:RNA | <50 | $T_R$*; 4xSSC | $T_R$*; 4xSSC |

‡The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
†SSPE (1xSSPE is 0.15M NaCl, 10 mM $NaH_2PO_4$, and 1.25 mM EDTA, pH 7.4) can be substituted for SSC (1xSSC is 0.15M NaCl and 15 mM sodium citrate) in the hybridization and wash buffers; washes are performed for 15 minutes after hybridization is complete.
*$T_B$-$T_R$: The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.) = 2(# of A + T bases) + 4(# of G + C bases). For hybrids between 18 and 49 base pairs in length, $T_m$(° C.) = 81.5 + 16.6($\log_{10}$[$Na^+$]) + 0.41(% G + C) − (600/N), where N is the number of bases in the hybrid, and [$Na^+$] is the concentration of sodium ions in the hybridization buffer ([$Na^+$] for 1xSSC = 0.165 M).

Additional examples of stringency conditions for polynucleotide hybridization are provided in Sambrook, J., E. F. Fritsch, and T. Maniatis, 1989, Molecular Cloning: A Labosequences are known in the art. General methods of expressing recombinant proteins are also known and are exemplified in R. Kaufman, Methods in Enzymology 185, 537-566

(1990). As defined herein "operably linked" means that the isolated polynucleotide of the invention and an expression control sequence are situated within a vector or cell in such a way that the protein is expressed by a host cell which has been transformed (transfected) with the ligated polynucleotide/ expression control sequence.

A number of types of cells may act as suitable host cells for expression of the protein. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it may be possible to produce the protein in lower eukaryotes such as yeast or in prokaryotes such as bacteria. Potentially suitable yeast strains include *Saccharomyces cerevisiae, Schizosaccharomyces pombe, Kluyveromyces* strains, *Candida*, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MAXBAC® kit), and such methods are well known in the art, as described in Summers and Smith, *Texas Agricultural Experiment Station Bulletin* No. 1555 (1987), incorporated herein by reference. As used herein, an insect cell capable of expressing a polynucleotide of the present invention is "transformed."

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, heparin-TOYOPEARL® or Cibacrom blue 3GA SEPHAROSE®; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of maltose binding protein (MBP), glutathione-S-transferase (GST) or thioredoxin (TRX). Kits for expression and purification of such fusion proteins are commercially available from New England BioLabs (Beverly, Mass.), Pharmacia (Piscataway, N.J.) and Invitrogen Corporation (Carlsbad, Calif.), respectively. The protein can also be tagged with an epitope and subsequently purified by using a specific antibody directed to such epitope. One such epitope ("Flag") is commercially available from the Eastman Kodak Company (New Haven, Conn.).

In addition, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The protein of the invention may also be expressed as a product of transgenic animals, e.g., as a component of the milk of transgenic cows, goats, pigs, or sheep which are characterized by somatic or germ cells containing a nucleotide sequence encoding the protein.

The protein may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with proteins may possess biological properties in common therewith, including protein activity. Thus, they may be employed as biologically active or immunological substitutes for natural, purified proteins in screening of therapeutic compounds and in immunological processes for the development of antibodies.

The proteins provided herein also include proteins characterized by amino acid sequences similar to those of purified proteins but into which modification are naturally provided or deliberately engineered. For example, modifications in the peptide or DNA sequences can be made by those skilled in the art using known techniques. Modifications of interest in the protein sequences may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein.

Other fragments and derivatives of the sequences of proteins which would be expected to retain protein activity in whole or in part and may thus be useful for screening or other immunological methodologies may also be easily made by those skilled in the art given the disclosures herein. Such modifications are believed to be encompassed by the present invention.

Uses and Biological Activity

The polynucleotides and proteins of the present invention can exhibit one or more of the uses or biological activities (including those associated with assays cited herein) identified below. Uses or activities described for proteins of the present invention may be provided by administration or use of such proteins or by administration or use of polynucleotides encoding such proteins (such as, for example, in gene therapies or vectors suitable for introduction of DNA).

hGL-19 Uses

Because of its homology to IL-10, human GIL-19/AE289 can be considered a member of the general family of cytokines and, as such, can exhibit similar activities to IL-10. Cytokines play important roles both in health and disease and have multiple clinical indications. Therefore this molecule (and other molecules of the present invention) will be useful as an agonist in certain clinical indications and antagonists of this molecule will be useful in other clinical situations, particularly in those in which IL-10 acts as an agonist or IL-10 antagonists act as an antagonist. Whether the agonist or antagonist is the preferred drug will depend on the particular aspects of the disease pathology, such as the cell types involved, the nature of the stimulus and the cellular microenvironment.

In a preferred embodiment, a hGIL-19 activity is at least one or more of the following activities: (1) modulating, for example antagonizing a signal transduction pathway (e.g. a GIL-19 dependant pathway); (2) modulating cytokine production and/or secretion (e.g. production and/or secretion of a proinflammatory cytokine); (3) modulating lymphokine production and/or secretion; (4) modulating production of adhesion molecules and/or cellular adhesion; (5) modulating expression or activity of nuclear transcription factors; (7) modulating secretion of IL-1; (8) competing with receptors for other cytokines; (9) competing with another hGIL-19 family member protein to bind a hGIL-19 receptor; (10) modulating nuclear translocation of internalized receptor for hGIL-19 or another cytokine or ligand-complexed receptor; (11) modulating cell proliferation, development or differentiation, for example, cytokine-stimulated or a hGIL-19 protein-stimulated proliferation, development or differentiation (e.g., of an epithelial cell, for example, a squamous epithelial cell of the esophagus, or of a skin cell, e.g., a keratinocyte); (12) modulating cell proliferation, development or differentiation of an osteogenic cell (e.g., of an osteoclast precursor cell, osteoclast and/or osteoblast); (13) modulating bone formation, bone metabolism and/or bone homeostasis (e.g., inhibiting bone resorption); (15) modulating cellular immune responses; (16) modulating cytokine-mediated proinflammatory actions (e.g., inhibiting acute phase protein synthesis by hepatocytes, fever, and/or prostaglandin synthesis, for example $PGE_2$ synthesis); and (17) promoting and/or potentiating wound healing.

Considering its apparent immunomodulatory role, human GIL-19/AE289 proteins may act on the following cell types: T cells, B cells, dendritic cells, macrophages/monocytes, neutrophils, mast cells, basophils, eosinophils, antigen presenting cells of the nervous system and antigen presenting cells of the kidney. Based on its homology to IL-10, human GIL-19/AE289 proteins (or agonists or antagonists thereof) can have the following activities and uses:

(a) Upregulation of humoral immune responses and attenuates cell mediated immune reactions;

(b) Function as an anti-inflammatory agent by inhibiting the synthesis of pro-inflammatory cytokines and chemokines;

(c) Modulation of inflammatory responses associated with injury, sepsis, gastrointestinal and cardiovascular disease, and inflammation following surgery;

(d) Treatment of acute myelogenous leukemia, Non-Hodgkin's lymphoma, bone marrow transplantation to treat recipient before engraftment, bone marrow transplantation to treat stem cells of donor before transplantation, and to ameliorate graft versus host disease following bone marrow transplantation;

(e) Treatment cell mediated autoimmune diseases such as multiple sclerosis, diabetes, rheumatoid arthritis, myasthenia gravis, systemic lupus erythematosus, nephrotoxicity associated with glomerulonephritis, inflammatory bowel disease, Crohn's disease, pancreatitis, and asthma.

Human GIL-19/AE289 agonists include without limitation human GIL-19/AE289 proteins and fragments, deletion mutants and addition mutants thereof; and peptide and small molecule compounds that interact with the receptor or other target to which human GIL-19/AE289 is directed. Human GIL-19/AE289 antagonists include without limitation antibodies directed to human GIL-19/AE289 proteins; soluble forms of the receptor or other target to which human GIL-19/AE289 is directed; antibodies directed to the receptor or other target to which human GIL-19/AE289 is directed; and peptide and small molecule compounds that inhibit or interfere with the interaction of human GIL-19/AE289 with its receptor or other target.

Research Uses and Utilities

The polynucleotides provided by the present invention can be used by the research community for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, those described in Gyuris et al., 1993, *Cell* 75: 791-803 and in Rossi et al., 1997, *Proc. Natl. Acad. Sci. USA* 94: 8405-8410, all of which are incorporated by reference herein) to identify polynucleotides encoding the other protein with which binding occurs or to identify inhibitors of the binding interaction.

The proteins provided by the present invention can similarly be used in assays to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

Nutritional Uses

Polynucleotides and proteins of the present invention can also be used as nutritional sources or supplements. Such uses include without limitation use as a protein or amino acid supplement, use as a carbon source, use as a nitrogen source and use as a source of carbohydrate. In such cases the protein or polynucleotide of the invention can be added to the feed of a particular organism or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

Cytokine and Cell Proliferation/Differentiation Activity

A protein of the present invention may exhibit cytokine, cell proliferation (either inducing or inhibiting) or cell differentiation (either inducing or inhibiting) activity or may induce production of other cytokines in certain cell populations. Many protein factors discovered to date, including all known cytokines, have exhibited activity in one or more factor-dependent cell proliferation assays, and hence the assays serve as a convenient confirmation of cytokine activity. The activity of a protein of the present invention is evidenced by any one of a number of routine factor dependent cell proliferation assays for cell lines including, without limitation, 32D, DA2, DA1G, T10, B9, B9/11, BaF3, MC9/G, M+ (preB M+), 2E8, RB5, DA1, 123, T1165, HT2, CTLL2, TF-1, Mo7e and CMK. The activity of a protein of the invention may, among other means, be measured by the following methods:

Assays for T-cell or thymocyte proliferation include without limitation those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1-3.19; Chapter 7, Immunologic studies in Humans); Takai et al., J. Immunol. 137: 3494-3500, 1986; Bertagnolli et al., J. Immunol. 145:1706-1712, 1990; Bertagnolli et al., Cellular Immunology 133: 327-341, 1991; Bertagnolli, et al., J. Immunol. 149:3778-3783, 1992; Bowman et al., J. Immunol. 152: 1756-1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In *Current Protocols in Immunology*. J. E. Coligan eds. Vol 1 pp. 3.12.1-3.12.14, John Wiley and Sons, Toronto. 1994; and Measurement of mouse and human Interferon γ, Schreiber, R. D. In *Current Protocols in Immunology*. J. E. Coligan eds. Vol 1 pp. 6.8.1-6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In *Current Protocols in Immunology*. J.E.e.a. Coligan eds. Vol 1 pp. 6.3.1-6.3.12, John Wiley and Sons, Toronto. 1991; deVries et al., J. Exp. Med. 173:1205-1211, 1991; Moreau et al., Nature 336:690-692, 1988; Greenberger et al., Proc. Natl. Acad. Sci. U.S.A. 80:2931-2938, 1983; Measurement of mouse and human interleukin 6-Nordan, R. In *Current Protocols in Immunology*. J.E.e.a. Coligan eds. Vol 1 pp. 6.6.1-6.6.5, John Wiley and Sons, Toronto. 1991; Smith et al., Proc. Natl. Acad. Sci. U.S.A. 83:1857-1861, 1986; Measurement of human Interleukin 11—Bennett, F., Giannotti, J., Clark, S. C. and Turner, K. J. In *Current Protocols in Immunology*. J.E.e.a. Coligan eds. Vol 1 pp. 6.15.1 John Wiley and Sons, Toronto. 1991; Measurement of mouse and human Interleukin 9—Ciarletta, A., Giannotti, J., Clark, S. C. and Turner, K. J. In *Current Protocols in Immunology*. J.E.e.a. Coligan eds. Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function; Chapter 6, Cytokines and their cellular receptors; Chapter 7, Immunologic studies in Humans); Weinberger et al., Proc. Natl. Acad. Sci. USA 77:6091-6095, 1980; Weinberger et al., Eur. J. Immun. 11:405-411, 1981; Takai et al., J. Immunol. 137:3494-3500, 1986; Takai et al., J. Immunol. 140:508-512, 1988.

Immune Stimulating or Suppressing Activity

A protein of the present invention may also exhibit immune stimulating or immune suppressing activity, including without limitation the activities for which assays are described herein. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases causes by viral, bacterial, fungal or other infection may be treatable using a protein of the present invention, including infections by HIV, hepatitis viruses, herpes viruses, mycobacteria, Leishmania spp., malaria spp. and various fungal infections such as candidiasis. Of course, in this regard, a protein of the present invention may also be useful where a boost to the immune system generally may be desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitis, myasthenia gravis, graft-versus-host disease and autoimmune inflammatory eye disease. Such a protein of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a protein of the present invention.

Using the proteins of the invention it may also be possible to regulate immune responses in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or energy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789-792 (1992) and Turka et al., Proc. Natl. Acad. Sci USA, 89:11102-11105 (1992). In addition, murine models of GVHD (see Paul ed., Fundamental Immunology, Raven Press, New York, 1989, pp. 846-847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells by disrupting receptor:ligand interactions of B lymphocyte antigens can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythmatosis in MRL/lpr/lpr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840-856).

Upregulation of an antigen function (preferably a B lymphocyte antigen function), as a means of up regulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. In addition, systemic viral diseases such as influenza, the common cold, and encephalitis might be alleviated by the administration of stimulatory forms of B lymphocyte antigens systemically.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing antiviral immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

In another application, up regulation or enhancement of antigen function (preferably B lymphocyte antigen function) may be useful in the induction of tumor immunity. Tumor cells (e.g., sarcoma, melanoma, lymphoma, leukemia, neuroblastoma, carcinoma) transfected with a nucleic acid encoding at least one peptide of the present invention can be administered to a subject to overcome tumor-specific tolerance in the subject. If desired, the tumor cell can be transfected to express a combination of peptides. For example, tumor cells obtained from a patient can be transfected ex vivo with an expression vector directing the expression of a peptide having B7-2-like activity alone, or in conjunction with a peptide having B7-1-like activity and/or B7-3-like activity. The transfected tumor cells are returned to the patient to result in expression of the peptides on the surface of the transfected cell. Alternatively, gene therapy techniques can be used to target a tumor cell for transfection in vivo.

The presence of the peptide of the present invention having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient amounts of MHC class I or MHC class II molecules, can be transfected with nucleic acid encoding all or a portion of (e.g., a cytoplasmic-domain truncated portion) of an MHC class I α chain protein and $\beta_2$ microglobulin protein or an MHC class II α chain protein and an MHC class II β chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of a protein of the invention may, among other means, be measured by the following methods:

Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1-3.19; Chapter 7, Immunologic studies in Humans); Herrmann et al., Proc. Natl. Acad. Sci. USA 78:2488-2492, 1981; Herrmann et al., J. Immunol. 128:1968-1974, 1982; Handa et al., J. Immunol. 135:1564-1572, 1985; Takai et al., J. Immunol. 137: 3494-3500, 1986; Takai et al., J. Immunol. 140:508-512, 1988; Herrmann et al., Proc. Natl. Acad. Sci. USA 78:2488-2492, 1981; Herrmann et al., J. Immunol. 128:1968-1974, 1982; Handa et al., J. Immunol. 135:1564-1572, 1985; Takai et al., J. Immunol. 137:3494-3500, 1986; Bowman et al., J. Virology 61:1992-1998; Takai et al., J. Immunol. 140:508-512, 1988; Bertagnolli et al., Cellular Immunology 133:327-341, 1991; Brown et al., J. Immunol. 153:3079-3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028-3033, 1990; and Assays for B cell function: In vitro antibody production, Mond, J. J. and Brunswick, M. In *Current Protocols in Immunology*. J.E.e.a. Coligan eds. Vol 1 pp. 3.8.1-3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1-3.19; Chapter 7, Immunologic studies in Humans); Takai et al., J. Immunol. 137:3494-3500, 1986; Takai et al., J. Immunol. 140:508-512, 1988; Bertagnolli et al., J. Immunol. 149:3778-3783, 1992.

Dendritic cell-dependent assays (which will identify, among others, proteins expressed by dendritic cells that activate naive T-cells) include, without limitation, those described in: Guery et al., J. Immunol. 134:536-544, 1995; Inaba et al., Journal of Experimental Medicine 173:549-559, 1991; Macatonia et al., Journal of Immunology 154:5071-5079, 1995; Porgador et al., Journal of Experimental Medicine 182:255-260, 1995; Nair et al., Journal of Virology 67:4062-4069, 1993; Huang et al., Science 264:961-965, 1994; Macatonia et al., Journal of Experimental Medicine 169:1255-1264, 1989; Bhardwaj et al., Journal of Clinical Investigation 94:797-807, 1994; and Inaba et al., Journal of Experimental Medicine 172:631-640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795-808, 1992; Gorczyca et al., Leukemia 7:659-670, 1993; Gorczyca et al., Cancer Research 53:1945-1951, 1993; Itoh et al., Cell 66:233-243, 1991; Zacharchuk, Journal of Immunology 145:4037-4045, 1990; Zamai et al., Cytometry 14:891-897, 1993; Gorczyca et al., International Journal of Oncology 1:639-648, 1992.

Assays for proteins that influence early steps of T-cell commitment and development include, without limitation, those described in: Antica et al., Blood 84:111-117, 1994; Fine et al., Cellular Immunology 155:111-122, 1994; Galy et al., Blood 85:2770-2778, 1995; Toki et al., Proc. Nat. Acad Sci. USA 88:7548-7551, 1991.

Hematopoiesis Regulating Activity

A protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelo-suppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

The activity of a protein of the invention may, among other means, be measured by the following methods:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al. Cellular Biology 15:141-151, 1995; Keller et al., Molecular and Cellular Biology 13:473-486, 1993; McClanahan et al., Blood 81:2903-2915, 1993.

Assays for stem cell survival and differentiation (which will identify, among others, proteins that regulate lympho-hematopoiesis) include, without limitation, those described in: Methylcellulose colony forming assays, Freshney, M. G. In *Culture of Hematopoietic Cells*. R. I. Freshney, et al. eds. Vol pp. 265-268, Wiley-Liss, Inc., New York, N.Y. 1994; Hirayama et al., Proc. Natl. Acad. Sci. USA 89:5907-5911, 1992; Primitive hematopoietic colony forming cells with high proliferative potential, McNiece, I. K. and Briddell, R. A. In *Culture of Hematopoietic Cells. R. I. Freshney, et al. eds. Vol* pp. 23-39, Wiley-Liss, Inc., New York, N.Y. 1994; Neben et al., Experimental Hematology 22:353-359, 1994; Cobblestone area forming cell assay, Ploemacher, R. E. In *Culture of Hematopoietic Cells*. R. I. Freshney, et al. eds. Vol pp. 1-21, Wiley-Liss, Inc., New York, N.Y. 1994; Long term bone marrow cultures in the presence of stromal cells, Spooncer, E., Dexter, M. and Allen, T. In *Culture of Hematopoietic Cells*. R. I. Freshney, et al. eds. Vol pp. 163-179, Wiley-Liss, Inc., New York, N.Y. 1994; Long term culture initiating cell assay, Sutherland, H. J. In *Culture of Hematopoietic Cells*. R. I. Freshney, et al. eds. Vol pp. 139-162, Wiley-Liss, Inc., New York, N.Y. 1994.

Tissue Growth Activity

A protein of the present invention also may have utility in compositions used for bone, cartilage, tendon, ligament and/or nerve tissue growth or regeneration, as well as for wound healing and tissue repair and replacement, and in the treatment of bums, incisions and ulcers.

A protein of the present invention, which induces cartilage and/or bone growth in circumstances where bone is not normally formed, has application in the healing of bone fractures and cartilage damage or defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein of this invention may also be used in the treatment of periodontal disease, and in other tooth repair processes. Such agents may provide an environment to attract bone-forming cells, stimulate growth of bone-forming cells or induce differentiation of progenitors of bone-forming cells. A protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendon/ligament formation. A protein of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide an environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a carrier as is well known in the art.

The protein of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a protein may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

Proteins of the invention may also be useful to promote better or faster closure of non-healing wounds, including without limitation pressure ulcers, ulcers associated with vascular insufficiency, surgical and traumatic wounds, and the like.

It is expected that a protein of the present invention may also exhibit activity for generation or regeneration of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Part of the desired effects may be by inhibition or modulation of fibrotic scarring to allow normal tissue to regenerate. A protein of the invention may also exhibit angiogenic activity.

A protein of the present invention may also be useful for gut protection or regeneration and treatment of lung or liver fibrosis, reperfusion injury in various tissues, and conditions resulting from systemic cytokine damage.

A protein of the present invention may also be useful for promoting or inhibiting differentiation of tissues described above from precursor tissues or cells; or for inhibiting the growth of tissues described above.

The activity of a protein of the invention may, among other means, be measured by the following methods:

Assays for tissue generation activity include, without limitation, those described in: International Patent Publication No. WO95/16035 (bone, cartilage, tendon); International Patent Publication No. WO95/05846 (nerve, neuronal);. International Patent Publication No. WO91/07491 (skin, endothelium).

Assays for wound healing activity include, without limitation, those described in: Winter, *Epidermal Wound Healing*, pps. 71-112 (Maibach, H I and Rovee, D T, eds.), Year Book Medical Publishers, Inc., Chicago, as modified by Eaglstein and Mertz, J. Invest. Dermatol 71:382-84 (1978).

Activin/Inhibin Activity

A protein of the present invention may also exhibit activin- or inhibin-related activities. Inhibins are characterized by their ability to inhibit the release of follicle stimulating hormone (FSH), while activins and are characterized by their ability to stimulate the release of follicle stimulating hormone (FSH). Thus, a protein of the present invention, alone or in heterodimers with a member of the inhibin a family, may be useful as a contraceptive based on the ability of inhibins to decrease fertility in female mammals and decrease spermatogenesis in male mammals. Administration of sufficient amounts of other inhibins can induce infertility in these mammals. Alternatively, the protein of the invention, as a homodimer or as a heterodimer with other protein subunits of the inhibin-β group, may be useful as a fertility inducing therapeutic, based upon the ability of activin molecules in stimulating FSH release from cells of the anterior pituitary. See, for example, U.S. Pat. No. 4,798,885. A protein of the invention may also be useful for advancement of the onset of fertility in sexually immature mammals, so as to increase the lifetime reproductive performance of domestic animals such as cows, sheep and pigs.

The activity of a protein of the invention may, among other means, be measured by the following methods:

Assays for activin/inhibin activity include, without limitation, those described in: Vale et al., Endocrinology 91:562-572, 1972; Ling et al., Nature 321:779-782, 1986; Vale et al., Nature 321:776-779, 1986; Mason et al., Nature 318:659-663, 1985; Forage et al., Proc. Natl. Acad. Sci. USA 83:3091-3095, 1986.

Chemotactic/Chemokinetic Activity

A protein of the present invention may have chemotactic or chemokinetic activity (e.g., act as a chemokine) for mammalian cells, including, for example, monocytes, fibroblasts, neutrophils, T-cells, mast cells, eosinophils, epithelial and/or endothelial cells. Chemotactic and chemokinetic proteins can be used to mobilize or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

The activity of a protein of the invention may, among other means, be measured by the following methods:

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 6.12, Measurement of alpha and beta Chemokines 6.12.1-6.12.28; Taub et al. J. Clin. Invest. 95:1370-1376, 1995; Lind et al. APMIS 103:140-146, 1995; Muller et al Eur. J. Immunol. 25: 1744-1748; Gruber et al. J. of Immunol. 152:5860-5867, 1994; Johnston et al. J. of Immunol. 153: 1762-1768, 1994.

Hemostatic and Thrombolytic Activity

A protein of the invention may also exhibit hemostatic or thrombolytic activity. As a result, such a protein is expected to be useful in treatment of various coagulation disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as, for example, infarction of cardiac and central nervous system vessels (e.g., stroke).

The activity of a protein of the invention may, among other means, be measured by the following methods:

Assay for hemostatic and thrombolytic activity include, without limitation, those described in: Linet et al., J. Clin. Pharmacol. 26:131-140, 1986; Burdick et al., Thrombosis Res. 45:413-419, 1987; Humphrey et al., Fibrinolysis 5:71-79 (1991); Schaub, Prostaglandins 35:467-474, 1988.

Receptor/Ligand Activity

A protein of the present invention may also demonstrate activity as receptors, receptor ligands or inhibitors or agonists of receptor/ligand interactions. Examples of such receptors and ligands include, without limitation, cytokine receptors and their ligands, receptor kinases and their ligands, receptor phosphatases and their ligands, receptors involved in cell-cell interactions and their ligands (including without limitation, cellular adhesion molecules (such as selectins, integrins and their ligands) and receptor/ligand pairs involved in antigen presentation, antigen recognition and development of cellular and humoral immune responses). Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

The activity of a protein of the invention may, among other means, be measured by the following methods:

Suitable assays for receptor-ligand activity include without limitation those described in: Current Protocols in Immunology, Ed by J. E. Coligan, A. M. Kruisbeek, D. H. Margulies, E. M. Shevach, W. Strober, Pub. Greene Publishing Associates and Wiley-lnterscience (Chapter 7.28, Measurement of Cellular Adhesion under static conditions 7.28.1-7.28.22), Takai et al., Proc. Natl. Acad. Sci. USA 84:6864-6868, 1987; Bierer et al., J. Exp. Med. 168:1145-1156, 1988; Rosenstein et al., J. Exp. Med. 169:149-160 1989; Stoltenborg et al., J. Immunol. Methods 175:59-68, 1994; Stitt et al., Cell 80:661-670, 1995.

Anti-Inflammatory Activity

Proteins of the present invention may also exhibit anti-inflammatory activity. The anti-inflammatory activity may be achieved by providing a stimulus to cells involved in the inflammatory response, by inhibiting or promoting cell-cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins exhibiting such activities can be used to treat inflammatory conditions including chronic or acute conditions), including without limitation inflammation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Proteins of the invention may also be useful to treat anaphylaxis and hypersensitivity to an antigenic substance or material.

Cadherin/Tumor Invasion Suppressor Activity

Cadherins are calcium-dependent adhesion molecules that appear to play major roles during development, particularly in defining specific cell types. Loss or alteration of normal cadherin expression can lead to changes in cell adhesion properties linked to tumor growth and metastasis. Cadherin malfunction is also implicated in other human diseases, such as pemphigus vulgaris and pemphigus foliaceus (auto-immune blistering skin diseases), Crohn's disease, and some developmental abnormalities.

The cadherin superfamily includes well over forty members, each with a distinct pattern of expression. All members of the superfamily have in common conserved extracellular repeats (cadherin domains), but structural differences are found in other parts of the molecule. The cadherin domains bind calcium to form their tertiary structure and thus calcium is required to mediate their adhesion. Only a few amino acids in the first cadherin domain provide the basis for homophilic adhesion; modification of this recognition site can change the specificity of a cadherin so that instead of recognizing only itself, the mutant molecule can now also bind to a different cadherin. In addition, some cadherins engage in heterophilic adhesion with other cadherins.

E-cadherin, one member of the cadherin superfamily, is expressed in epithelial cell types. Pathologically, if E-cadherin expression is lost in a tumor, the malignant cells become invasive and the cancer metastasizes. Transfection of cancer cell lines with polynucleotides expressing E-cadherin has reversed cancer-associated changes by returning altered cell shapes to normal, restoring cells' adhesiveness to each other and to their substrate, decreasing the cell growth rate, and drastically reducing anchorage-independent cell growth. Thus, reintroducing E-cadherin expression reverts carcinomas to a less advanced stage. It is likely that other cadherins have the same invasion suppressor role in carcinomas derived from other tissue types. Therefore, proteins of the present invention with cadherin activity, and polynucleotides of the present invention encoding such proteins, can be used to treat cancer. Introducing such proteins or polynucleotides into cancer cells can reduce or eliminate the cancerous changes observed in these cells by providing normal cadherin expression.

Cancer cells have also been shown to express cadherins of a different tissue type than their origin, thus allowing these cells to invade and metastasize in a different tissue in the body. Proteins of the present invention with cadherin activity, and polynucleotides of the present invention encoding such proteins, can be substituted in these cells for the inappropriately expressed cadherins, restoring normal cell adhesive properties and reducing or eliminating the tendency of the cells to metastasize.

Additionally, proteins of the present invention with cadherin activity, and polynucleotides of the present invention encoding such proteins, can used to generate antibodies recognizing and binding to cadherins. Such antibodies can be used to block the adhesion of inappropriately expressed tumor-cell cadherins, preventing the cells from forming a tumor elsewhere. Such an anti-cadherin antibody can also be used as a marker for the grade, pathological type, and prognosis of a cancer, i.e. the more progressed the cancer, the less cadherin expression there will be, and this decrease in cadherin expression can be detected by the use of a cadherin-binding antibody.

Fragments of proteins of the present invention with cadherin activity, preferably a polypeptide comprising a decapeptide of the cadherin recognition site, and poly-nucleotides of the present invention encoding such protein fragments, can also be used to block cadherin function by binding to cadherins and preventing them from binding in ways that produce undesirable effects. Additionally, fragments of proteins of the present invention with cadherin activity, preferably truncated soluble cadherin fragments which have been found to be stable in the circulation of cancer patients, and polynucleotides encoding such protein fragments, can be used to disturb proper cell-cell adhesion.

Assays for cadherin adhesive and invasive suppressor activity include, without limitation, those described in: Hortsch et al. J Biol Chem 270 (32): 18809-18817, 1995; Miyaki et al. Oncogene 11: 2547-2552, 1995; Ozawa et al. Cell 63: 1033-1038, 1990.

Tumor Inhibition Activity

In addition to the activities described above for immunological treatment or prevention of tumors, a protein of the invention may exhibit other anti-tumor activities. A protein may inhibit tumor growth directly or indirectly (such as, for example, via antibody-dependent cell-mediated cytotoxicity (ADCC)). A protein may exhibit its tumor inhibitory activity by acting on tumor tissue or tumor precursor tissue, by inhibiting formation of tissues necessary to support tumor growth (such as, for example, by inhibiting angiogenesis), by causing production of other factors, agents or cell types which inhibit tumor growth, or by suppressing, eliminating or inhibiting factors, agents or cell types which promote tumor growth.

Other Activities

A protein of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or caricadic cycles or rhythms; effecting the fertility of male or female subjects; effecting the metabolism, catabolism, anabolism, processing, utilization, storage or elimination of dietary fat, lipid, protein, carbohydrate, vitamins, minerals, cofactors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

Administration and Dosing

A protein of the present invention (from whatever source derived, including without limitation from recombinant and non-recombinant sources) may be used in a pharmaceutical composition when combined with a pharmaceutically acceptable carrier. Such a composition may also contain (in addition to protein and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IFN, TNF0, TNF1, TNF2, G-CSF, Meg-CSF, thrombopoietin, stem cell factor, and erythropoietin. The pharmaceutical composition may further contain other agents which either enhance the activity of the protein or compliment its activity or use in treatment. Such additional factors and/or agents may be included in the pharmaceutical composition to produce a synergistic effect with protein of the invention, or to minimize side effects. Conversely, protein of the present invention may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

A protein of the present invention may be active in multimers (e.g., heterodimers or homodimers) or complexes with itself or other proteins. As a result, pharmaceutical compositions of the invention may comprise a protein of the invention in such multimeric or complexed form.

The pharmaceutical composition of the invention may be in the form of a complex of the protein(s) of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunolgobulin and other molecules on B cells as well as antibodies able to bind the TCR and other molecules on T cells can be combined with the pharmaceutical composition of the invention.

The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of protein of the present invention is administered to a mammal having a condition to be treated. Protein of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, protein of the present invention may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering protein of the present invention in combination with cytokine(s), lymphokine(s), other hematopoietic factor(s), thrombolytic or anti-thrombotic factors.

Administration of protein of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection. Intravenous administration to the patient is preferred.

When a therapeutically effective amount of protein of the present invention is administered orally, protein of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein of the present invention, and preferably from about 25 to 90% protein of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein of the present invention, and preferably from about 1 to 50% protein of the present invention.

When a therapeutically effective amount of protein of the present invention is administered by intravenous, cutaneous or subcutaneous injection, protein of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of protein of the present invention in the pharmaceutical composition of the present invention will depend upon the nature and severity of the condition being treated, and on the nature of prior treatments which the patient has undergone. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further. It is contemplated that the various pharmaceutical compositions used to practice the method of the present invention should contain about 0.01 µg to about 100 mg (preferably about 0.1 ng to about 10 mg, more preferably about 0.1 µg to about 1 mg) of protein of the present invention per kg body weight.

The duration of intravenous therapy using the pharmaceutical composition of the present invention will vary, depending on the severity of the disease being treated and the condition and potential idiosyncratic response of each individual patient. It is contemplated that the duration of each application of the protein of the present invention will be in the range of 12 to 24 hours of continuous intravenous administration. Ultimately the attending physician will decide on the appropriate duration of intravenous therapy using the pharmaceutical composition of the present invention.

Protein of the invention may also be used to immunize animals to obtain polyclonal and monoclonal antibodies which specifically react with the protein. As used herein, the term "antibody" includes without limitation a polyclonal antibody, a monoclonal antibody, a chimeric antibody, a single-chain antibody, a CDR-grafted antibody, a humanized antibody, or fragments thereof which bind to the indicated protein. Such term also includes any other species derived from an antibody or antibody sequence which is capable of binding the indicated protein.

Antibodies to a particular protein can be produced by methods well known to those skilled in the art. For example, monoclonal antibodies can be produced by generation of antibody-producing hybridomas in accordance with known methods (see for example, Goding, 1983, Monoclonal antibodies: principles and practice, Academic Press Inc., New York; and Yokoyama, 1992, "Production of Monoclonal Antibodies" in Current Protocols in Immunology, Unit 2.5, Greene Publishing Assoc. and John Wiley & Sons). Polyclonal sera and antibodies can be produced by inoculation of a mammalian subject with the relevant protein or fragments thereof in accordance with known methods. Fragments of antibodies, receptors, or other reactive peptides can be produced from the corresponding antibodies by cleavage of and collection of the desired fragments in accordance with known methods (see for example, Goding, supra; and Andrew et al., 1992, "Fragmentation of Immunoglobulins" in Current Protocols in Immunology, Unit 2.8, Greene Publishing Assoc. and John Wiley & Sons). Chimeric antibodies and single chain antibodies can also be produced in accordance with known recombinant methods (see for example, U.S. Pat. Nos. 5,169,939, 5,194,594, and 5,576,184). Humanized antibodies can also be made from corresponding murine antibodies in accordance with well known methods (see for example, U.S. Pat. Nos. 5,530,101, 5,585,089, and 5,693,762). Additionally, human antibodies may be produced in non-human animals such as mice that have been genetically altered to express human antibody molecules (see for example Fishwild et al., 1996, *Nature Biotechnology* 14: 845-851; Mendez et al., 1997, *Nature Genetics* 15: 146-156 (erratum *Nature Genetics* 16: 410); and U.S. Pat. Nos. 5,877,397 and 5,625,126). Such antibodies may be obtained using either the entire protein or fragments thereof as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer. Chem. Soc. 85, 2149-2154 (1963); J. L. Krstenansky, et al., FEBS Lett. 211, 10 (1987).

Monoclonal antibodies binding to the protein of the invention may be useful diagnostic agents for the immunodetection of the protein. Neutralizing monoclonal antibodies binding to the protein may also be useful therapeutics for both conditions associated with the protein and also in the treatment of some forms of cancer where abnormal expression of the protein is involved. In the case of cancerous cells or leukemic cells, neutralizing monoclonal antibodies against the protein may be useful in detecting and preventing the metastatic spread of the cancerous cells, which may be mediated by the protein.

For compositions of the present invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a protein of the invention which may also optionally be included in the composition as described above, may alternatively or additionally, be administered simultaneously or sequentially with the composition in the methods of the invention. Preferably for bone and/or cartilage formation, the composition would include a matrix capable of delivering the protein-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalciumphosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the protein compositions from disassociating from the matrix.

A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5-20 wt %, preferably 1-10 wt % based on total formulation weight, which represents the amount necessary to prevent desorbtion of the protein from the polymer matrix and to provide appropriate handling of the composition, yet not so much that the progenitor cells are prevented from infiltrating the matrix, thereby providing the protein the opportunity to assist the osteogenic activity of the progenitor cells.

In further compositions, proteins of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-α and TGF-β), and insulin-like growth factor (IGF).

The therapeutic compositions are also presently valuable for veterinary applications. Particularly domestic animals and thoroughbred horses, in addition to humans, are desired patients for such treatment with proteins of the present invention.

The dosage regimen of a protein-containing pharmaceutical composition to be used in tissue regeneration will be determined by the attending physician considering various factors which modify the action of the proteins, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA).

Cells may also be cultured ex vivo in the presence of proteins of the present invention in order to proliferate or to produce a desired effect on or activity in such cells. Treated cells can then be introduced in vivo for therapeutic purposes.

This invention is further illustrated by the following examples which should not be construed as limiting. The contents of all references, patents and published patent applications cited throughout this application, as well as the Sequence Listing, are incorporated herein by reference.

EXAMPLES

Identification and Characterization of Clone "hGIL-19/AE289"

A polynucieotide of the present invention has been identified as clone "HGIL-19/AE289". Clone hGIL-19/AE289 was isolated according to the following method. A murine EST was identified from a murine cDNA library made from splenocytes activated with both ConA and bone marrow derived dendritic cells. The EST was identified using methods which are selective for cDNAs encoding secreted proteins (see U.S. Pat. No. 5,536,637). The murine EST sequence was used to isolate a fill-length murine clone from the same cDNA library. Analysis of the sequence of the murine clone revealed a significant homology to interleukin-10 (IL-10).

In order to isolate a human homolog of the murine clone, PCR primers were constructed based upon the region of the murine sequence which showed homology to IL-10. Use of such primers for amplification in a human PBMC library produced a PCR product of significant size. Analysis of the sequence of the PCR product confirmed that it was a homolog of the murine cDNA. Oligonucleotides were constructed from the sequence of the partial human clone and used to isolate a full-length human clone from the PBMC library.

hGIL-19/AE289 is a full-length human clone, including the entire coding sequence of a secreted protein (also referred to herein as "hGIL-19/AE289" protein). Analysis of its amino acid sequence indicated that it has about 23% homology to hIL-10. Based on the putative receptor-binding motifs in IL-10, three motifs involved with analogous function have been proposed in HGIL-19/AE289 through computer modeling. These are the regions of SEQ ID NO:2 from residue 50 to 60, from residue 63 to 81, and from residue 168 to 177. Analyses of databases revealed that hGIL-19 also exhibits similar levels of homology with IL-10 of other species.

The nucleotide sequence of hGIL-19/AE289 as presently determined is reported in SEQ ID NO:1, and includes a poly (A) tail. The amino acid sequence of the hGIL-19/AE289 protein corresponding to the foregoing nucleotide sequence is reported in SEQ ID NO:2.

Characterization of hGIL-19/AE289 protein

Cell lines which stably express and secrete full length hGIL-19/AE289 protein were created by transfecting CHO cells with hGIL-19/AE289 cDNA in appropriate expression vectors. Transiently transfected COS cells using appropriate hGIL-19/AE289 expression vectors have been used to make hGIL-19/AE289 protein for analysis. Transfections were accomplished using the commercially available Lipofectamine reagent (Gibco). Interestingly, COS cells which express hGIL-19 were observed to non-uniformly detach, forming holes in the cell culture monolayer. Media conditioned by transfected COS cells was used to demonstrate cytokine-like activity of hGIL-19/AE289 protein. Western blot analysis of cell lysates showed that Stat-3 becomes phosphorylated (activated) in a kidney mesangial tissue-derived cell line exhibiting macrophage-like qualities (MES-13; see, Dumoutier et al (2000) *J. of Immunology* 164:1814-1819) upon exposure of that cell to media conditioned by hGIL-19/AE289-expressing cells. In addition phosphorylation of Stat-3 is induced in non-transfected COS cells that are treated with hGIL-19 protein.

Electrophoretic analysis of hGIL-19/AE289 protein (derived from the transfected COS cell lines described herein) indicated that the expressed protein exists in a range of sizes. Treatment of COS-derived hGIL-19 protein with N-glycanase prior to electrophoresis results in a single band corresponding to the highest mobility (e.g. lowest molecular weight) species seen in untreated hGIL-19/AE289. This is consistent with proposed glycosylation events which may occur at the putative N-linked glycosylation sites identified in the amino acid sequence of hGIL-19/AE289 (amino acid residues 54-56, 68-70, 97-99, and 176-178 of SEQ ID NO:2).

Edman N-terminal sequencing determined that the N-terminus of the mature hGIL-19/AE289 protein begins with the residue at position 34 of SEQ ID NO:2 (alanine). Expression vectors were created which fuse a "6× histidine" affinity tag and a FLAG epitope tag to the N-terminus of the mature hGIL-19/AE289 protein. (The added amino acid tag is given in SEQ ID NO:3 and has the following amino acid sequence:

```
MKFLVNVALVFMVVYISYIYAGSGHHHHHHGSGDYKDDDDKA
PISSHCR).
```

These tagged constructs were used to create stably expressing CHO cell lines and transiency expressing COS cell lines. The tags provided a convenient means for detecting hGIL-19/AE289 (e.g. anti-6xhis antibodies; anti-FLAG antibodies), and for purifying the protein from conditioned media (using $Ni^{+2}$ resin). Human GIL-19 protein purified by this tag from the hGIL-19/AE289-expressing COS cell lines could used to induce Stat-3 activation in MES-13 cells.

Comparison of hGIL-19 mRNA transcripts in activated Th1 and Th2 cells (see, for example, Syrbe et al, (1999) *Springer Seminars in Immunopathology,* 21:263-85) indicated a substantially higher level of expression of GIL-19 in activated Th1 cells than in activated Th2 cells. Analysis of GIL-19 mRNA was accomplished with RNAse protection assays.

Immunological Effects GIL-19

The immunological effects of GIL-19 were investigated in a metazoan context by viral introduction of the cDNA of murine GIL-19 into mice. An adenoviral vector was used to express a cDNA of murine GIL-19 in 8 week old C57/B6 female mice by injection of $5 \times 10^{10}$ viral particles. Test mice were sacrificed at 7 and 14 days after injection and compared with control mice injected with buffer only or with adenovirus expressing green fluorescent protein (GFP). At days 7 and 14, it was noted that the absolute and relative thymic weights were significantly decreased in the mice which expressed the viral murine GIL-19. Absolute mean weight of the spleen was decreased on day 14 and liver weights were slightly increased on day 7. A gross generalized atrophy of the thymus as well as lymphoid depletion (observed microscopically) was apparent on days 7 and 14.

In addition, there were a number of hematological effects that were apparent on day 7, including decreased red blood cell count, hemoglobin, and hematocrit. These effects, taken together, indicated anemia in the animals. Furthermore, there was an increase in platelets as well as an increase in the white blood cell count due to an increase of neutrophils. In light of these observations there was no evidence of a regenerative response, which indicated that the effects may be at the level of the bone marrow.

Furthermore, there was a slight decrease in Albumin levels at day 7 and day 14. A possible cause for this is the loss of small molecules through the kidney or gut.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated polynucleotide, comprising a nucleic acid sequence that hybridizes under conditions at least as stringent as 4×SSC at 65 degrees C. followed by washes at 65 degrees C. in 1×SSC, or 4×SSC with 50% formamide at 42 degrees C. followed by washes at 65 degrees C. in 1×SSC, to a complement of the polynucleotide having the nucleotide sequence of SEQ ID NO:1, wherein said nucleic acid sequence encodes a polypeptide that induces phosphorylation of a Stat3 polypeptide; and wherein the polypeptide encoded by the nucleic acid sequence comprises at least one amino acid sequence selected from: amino acids 50-60 of SEQ ID NO:2, amino acids 63-81 of SEQ ID NO:2, and amino acids 168-177 of SEQ ID NO:2.

2. The polynucleotide of claim 1 wherein said polynucleotide is operably linked to at least one expression control sequence.

3. A cultured host cell transformed with the polynucleotide of claim 2.

4. The cultured host cell of claim 3, wherein said cell is a mammalian cell.

5. A process for producing a polypeptide encoded by the polynucleotide of claim 2, which comprises:
   (a) growing a culture of a cultured host cell transformed with the polynucleotide of claim 2 in a suitable culture medium; and
   (b) purifying said polypeptide from the culture.

6. An isolated polynucleotide, comprising a nucleic acid sequence that encodes a protein that shares at least 95% sequence identity with the protein having the amino acid sequence of SEQ ID NO:2, wherein said nucleic acid sequence encodes a polypeptide that induces phosphorylation of a Stat3 polypeptide; and wherein the polypeptide encoded by the nucleic acid sequence comprises at least one amino acid sequence selected from: amino acids 50-60 of SEQ ID NO:2, amino acids 63-81 of SEQ ID NO:2, and amino acids 168-177 of SEQ ID NO:2.

7. The polynucleotide of claim 6 wherein said polynucleotide is operably linked to at least one expression control sequence.

8. A cultured host cell transformed with the polynucleotide of claim 7.

9. The cultured host cell of claim 8, wherein said cell is a mammalian cell.

10. A process for producing a polypeptide encoded by the polynucleotide of claim 7, which comprises:

(a) growing a culture of a cultured host cell transformed with the polynucleotide of claim 7 in a suitable culture medium; and (b) purifying said polypeptide from the culture.

11. The polynucleotide of claim 1, wherein the nucleic acid sequence is at least 95% identical to SEQ ID NO:1.

* * * * *

UNITED STATES PATENT AND TRADEMARK OFFICE
CERTIFICATE OF CORRECTION

| | | |
|---|---|---|
| PATENT NO. | : 7,585,646 B2 | Page 1 of 1 |
| APPLICATION NO. | : 11/013920 | |
| DATED | : September 8, 2009 | |
| INVENTOR(S) | : Kenneth Jacobs et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 573 days.

Signed and Sealed this

Fifteenth Day of February, 2011

David J. Kappos
*Director of the United States Patent and Trademark Office*

SEQUENCE LISTING

```
<160> NUMBER OF SEQ ID NOS: 2

<210> SEQ ID NO 1
<211> LENGTH: 1177
<212> TYPE: DNA
<213> ORGANISM: Homo sapiens

<400> SEQUENCE: 1
ggccaaagag gcctacaggt tctccttccc cagtcaccag ttgctcgagt tagaattgtc      60
tgcaatggcc gccctgcaga aatctgtgag ctctttcctt atggggaccc tggccaccag     120
ctgcctcctt ctcttggccc tcttggtaca gggaggagca gctgcgccca tcagctccca     180
ctgcaggctt gacaagtcca acttccagca gccctatatc accaaccgca ccttcatgct     240
ggctaaggag gctagcttgg ctgataacaa cacagacgtt cgtctcattg gggagaaact     300
gttccacgga gtcagtatga gtgagcgctg ctatctgatg aagcaggtgc tgaacttcac     360
ccttgaagaa gtgctgttcc ctcaatctga taggttccag ccttatatgc aggaggtggt     420
gcccttcctg gccaggctca gcaacaggct aagcacatgt catattgaag gtgatgacct     480
gcatatccag aggaatgtgc aaaagctgaa ggacacagtg aaaaagcttg gagagagtgg     540
agagatcaaa gcaattggag aactggattt gctgtttatg tctctgagaa atgcctgcat     600
ttgaccagag caaagctgaa aaatgaataa ctaaccccct ttccctgcta gaaataacaa     660
ttagatgccc caaagcgatt ttttttaacc aaaaggaaga tgggaagcca aactccatca     720
tgatgggtgg attccaaatg aacccctgcg ttagttacaa aggaaaccaa tgccactttt     780
gtttataaga ccagaaggta gactttctaa gcatagatat ttattgataa catttcattg     840
taactggtgt tctatacaca gaaaacaatt tatttttaa ataattgtct ttttccataa     900
```

```
aaaagattac tttccattcc tttaggggaa aaaacccta aatagcttca tgtttccata    960
atcagtactt tatatttata aatgtattta ttattattat aagactgcat tttatttata   1020
tcattttatt aatatggatt tatttataga aacatcattc gatattgcta cttgagtgta   1080
aggctaatat tgatatttat gacaataatt atagagctat aacatgttta tttgacctca   1140
ataaacactt ggatatccta aaaaaaaaaa aaaaaaa                            1177

<210> SEQ ID NO 2
<211> LENGTH: 179
<212> TYPE: PRT
<213> ORGANISM: Homo sapiens

<400> SEQUENCE: 2

Met Ala Ala Leu Gln Lys Ser Val Ser Ser Phe Leu Met Gly Thr Leu
 1               5                  10                  15

Ala Thr Ser Cys Leu Leu Leu Ala Leu Leu Val Gln Gly Gly Ala
            20                  25                  30

Ala Ala Pro Ile Ser Ser His Cys Arg Leu Asp Lys Ser Asn Phe Gln
        35                  40                  45

Gln Pro Tyr Ile Thr Asn Arg Thr Phe Met Leu Ala Lys Glu Ala Ser
    50                  55                  60

Leu Ala Asp Asn Asn Thr Asp Val Arg Leu Ile Gly Glu Lys Leu Phe
65                  70                  75                  80

His Gly Val Ser Met Ser Glu Arg Cys Tyr Leu Met Lys Gln Val Leu
                85                  90                  95

Asn Phe Thr Leu Glu Glu Val Leu Phe Pro Gln Ser Asp Arg Phe Gln
               100                 105                 110

Pro Tyr Met Gln Glu Val Val Pro Phe Leu Ala Arg Leu Ser Asn Arg
           115                 120                 125

Leu Ser Thr Cys His Ile Glu Gly Asp Asp Leu His Ile Gln Arg Asn
       130                 135                 140

Val Gln Lys Leu Lys Asp Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Ile
```